US009826958B2

(12) United States Patent
Zhang et al.

(10) Patent No.: US 9,826,958 B2
(45) Date of Patent: Nov. 28, 2017

(54) AUTOMATED DETECTION OF SUSPECTED ABNORMALITIES IN ULTRASOUND BREAST IMAGES

(71) Applicants: Wei Zhang, San Jose, CA (US); Shih-Ping Wang, Los Altos, CA (US); Alexander Schneider, Los Altos, CA (US); Nico Karssemeijer, Beek-Ubbergen (NL)

(72) Inventors: Wei Zhang, San Jose, CA (US); Shih-Ping Wang, Los Altos, CA (US); Alexander Schneider, Los Altos, CA (US); Nico Karssemeijer, Beek-Ubbergen (NL)

(73) Assignee: QView, INC, Los Altos, CA (US)

( * ) Notice: Subject to any disclaimer, the term of this patent is extended or adjusted under 35 U.S.C. 154(b) by 0 days.

(21) Appl. No.: 14/044,842

(22) Filed: Oct. 2, 2013

(65) Prior Publication Data
US 2014/0039318 A1    Feb. 6, 2014

Related U.S. Application Data

(63) Continuation-in-part of application No. 12/839,371, filed on Jul. 19, 2010, and a continuation-in-part of
(Continued)

(51) Int. Cl.
*A61B 8/08*    (2006.01)
*G06T 7/00*    (2017.01)

(52) U.S. Cl.
CPC .......... *A61B 8/0825* (2013.01); *A61B 8/5238* (2013.01); *G06T 7/0012* (2013.01);
(Continued)

(58) Field of Classification Search
CPC ....... A61B 8/4477; A61B 8/447; A61B 6/502; A61B 6/5247; A61B 2576/00;
(Continued)

(56) References Cited

U.S. PATENT DOCUMENTS 4,058,001 A  *  11/1977  Waxman ................... 600/443
5,433,218 A      7/1995  Wildermeersch
(Continued)

FOREIGN PATENT DOCUMENTS

WO   PCT/US13/63149    4/2014
WO   WO2015017542     2/2015
WO   WO2015084681     6/2015

OTHER PUBLICATIONS

International Search Report of International Application No. PCT/US13/63149 dated Dec. 23, 2013.
(Continued)

*Primary Examiner* — Victoria P Shumate
*Assistant Examiner* — Teresa Williams
(74) *Attorney, Agent, or Firm* — Cooper & Dunham LLP

(57) ABSTRACT

A method and system for processing and displaying breast ultrasound information is described. A 2D feature weighted volumetric coronal image as a "guide" or "road map" is generated from the 3D ultrasound data volume to represent the 3D dataset with the goal of emphasizing abnormalities within the breast while excluding non-breast structures, particularly those external to the breast such as ribs and chest wall.

3 Claims, 9 Drawing Sheets

Related U.S. Application Data application No. PCT/US2009/066020, filed on Nov. 27, 2009.

(60) Provisional application No. 61/860,900, filed on Jul. 31, 2013, provisional application No. 61/830,241, filed on Jun. 3, 2013, provisional application No. 61/728,166, filed on Nov. 19, 2012, provisional application No. 61/709,136, filed on Oct. 2, 2012.

(52) U.S. Cl.
CPC ........... *G06T 2207/10132* (2013.01); *G06T 2207/30068* (2013.01)

(58) Field of Classification Search
CPC ..... A61B 8/0825; A61B 8/469; A61B 8/5223; G06T 2207/10132; G06T 15/005; G06T 2207/30068
USPC ........ 382/128, 131; 600/300, 407, 427, 437, 600/440, 445
See application file for complete search history.

(56) References Cited

U.S. PATENT DOCUMENTS

| | | | |
|---|---|---|---|
| 5,709,206 A * | 1/1998 | Teboul | 600/437 |
| 6,167,296 A * | 12/2000 | Shahidi | 600/427 |
| 6,317,617 B1 * | 11/2001 | Gilhuijs | A61B 5/055 128/922 |
| 6,396,940 B1 * | 5/2002 | Carrott et al. | 382/128 |
| 6,450,962 B1 * | 9/2002 | Brandl | G01S 15/8993 600/440 |
| 6,511,426 B1 * | 1/2003 | Hossack et al. | 600/437 |
| 6,520,913 B1 * | 2/2003 | Pesavento et al. | 600/438 |
| 6,574,499 B1 * | 6/2003 | Dines et al. | 600/427 |
| 6,733,458 B1 * | 5/2004 | Steins et al. | 600/461 |
| 6,876,879 B2 * | 4/2005 | Dines et al. | 600/427 |
| 6,878,796 B2 * | 4/2005 | Leonte | C08J 3/095 257/E21.259 |
| 7,004,904 B2 * | 2/2006 | Chalana et al. | 600/443 |
| 7,519,209 B2 * | 4/2009 | Dawant et al. | 382/128 |
| 7,597,663 B2 * | 10/2009 | Wang et al. | 600/437 |
| 7,615,008 B2 * | 11/2009 | Zhang et al. | 600/437 |
| 7,616,801 B2 * | 11/2009 | Gkanatsios et al. | 382/132 |
| 7,640,050 B2 * | 12/2009 | Glenn et al. | 600/407 |
| 7,828,733 B2 * | 11/2010 | Zhang et al. | 600/437 |
| 8,096,949 B2 | 1/2012 | Chen | |
| 8,131,049 B2 * | 3/2012 | Ruth | G06K 9/4638 382/131 |
| 8,150,128 B2 | 4/2012 | Konofagou | |
| 8,576,911 B2 | 11/2013 | Seong | |
| 8,977,052 B2 | 3/2015 | Seong | |
| 9,025,858 B2 | 5/2015 | Seong | |
| 9,084,578 B2 | 7/2015 | Seong | |
| 9,202,279 B2 | 12/2015 | Seong | |
| 9,305,349 B2 | 4/2016 | Seong | |
| 9,361,685 B2 | 6/2016 | Seong | |
| 2005/0228250 A1 * | 10/2005 | Bitter et al. | 600/407 |
| 2006/0173303 A1 * | 8/2006 | Yu et al. | 600/437 |
| 2007/0038085 A1 * | 2/2007 | Zhang et al. | 600/437 |
| 2008/0155451 A1 * | 6/2008 | Lundstrom | G06F 19/321 715/772 |
| 2008/0285819 A1 * | 11/2008 | Konofagou et al. | 382/128 |
| 2008/0292164 A1 * | 11/2008 | Azar et al. | 382/131 |
| 2009/0080765 A1 * | 3/2009 | Bernard | G06T 11/006 382/154 |
| 2010/0280375 A1 | 11/2010 | Zhang | |
| 2012/0189178 A1 | 7/2012 | Seong | |
| 2013/0022253 A1 | 1/2013 | Seong | |
| 2013/0030278 A1 | 1/2013 | Seong | |
| 2013/0094766 A1 | 4/2013 | Seong | |
| 2013/0114904 A1 | 5/2013 | Seong | |
| 2013/0116535 A1 | 5/2013 | Seong | |
| 2013/0245426 A1 | 9/2013 | Seong | |
| 2014/0037159 A1 | 2/2014 | Seong | |
| 2014/0101080 A1 | 4/2014 | Seong | |
| 2014/0105473 A1 | 4/2014 | Seong | |
| 2014/0105474 A1 | 4/2014 | Seong | |
| 2014/0122515 A1 | 5/2014 | Seong | |
| 2014/0142413 A1 | 5/2014 | Seong | |
| 2014/0153807 A1 | 6/2014 | Seong | |
| 2014/0185900 A1 | 7/2014 | Seong | |
| 2014/0193051 A1 | 7/2014 | Seong | |
| 2014/0194722 A1 | 7/2014 | Seong | |
| 2014/0200452 A1 | 7/2014 | Seong | |
| 2014/0228687 A1 | 8/2014 | Seong | |
| 2014/0241606 A1 | 8/2014 | Seong | |
| 2014/0343420 A1 | 11/2014 | Zhang et al. | |
| 2015/0003677 A1 | 1/2015 | Seong | |
| 2015/0087979 A1 | 3/2015 | Zhang et al. | |
| 2015/0146958 A1 | 5/2015 | Seong | |
| 2015/0157298 A1 | 6/2015 | Seong | |
| 2015/0173705 A1 | 6/2015 | Seong | |
| 2015/0187071 A1 | 7/2015 | Seong | |
| 2015/0230773 A1 | 8/2015 | Seong | |
| 2015/0254846 A1 | 9/2015 | Seong | |
| 2015/0265251 A1 | 9/2015 | Seong | |
| 2015/0302583 A1 | 10/2015 | Seong | |
| 2015/0317794 A1 | 11/2015 | Seong | |
| 2015/0339859 A1 | 11/2015 | Seong | |
| 2016/0019320 A1 | 1/2016 | Seong | |
| 2016/0019441 A1 | 1/2016 | Seong | |
| 2016/0042525 A1 | 2/2016 | Seong | |
| 2016/0171299 A1 | 6/2016 | Seong | |

OTHER PUBLICATIONS

Notice of References in U.S. Appl. No. 14/044,842 dated Jul. 16, 2015.

Notice of References in U.S. Appl. No. 14/044,842 dated Sep. 8, 2014.

* cited by examiner

US 9,826,958 B2

AUTOMATED DETECTION OF SUSPECTED ABNORMALITIES IN ULTRASOUND BREAST IMAGES

REFERENCE TO RELATED APPLICATIONS

This patent application claims the benefit of and incorporates by reference each of the following applications:
U.S. Prov. Ser. No. 61/709,136 filed Oct. 2, 2012;
U.S. Prov. Ser. No. 61/728,166 filed on Nov. 19, 2012;
U.S. Prov. Ser. No. 61/830,241 filed on Jun. 3, 2013; and
U.S. Prov. Ser. No. 61/860,900 filed on Jul. 31, 2013.

This application is a continuation-in-part of and incorporated by reference each of the following applications:
U.S. Ser. No. 2012/0014578 filed on Jul. 19, 2010; and
International Patent Application No. WO 2011/065950 A1 filed on Nov. 27, 2009.

FIELD

The method and system described in this patent specification relate to displaying 3D breast ultrasound images and other information in a manner believed to better assist their reading and interpretation by physicians or other users of the method and system. More specifically, the patent specification relates to a method and system of displaying a feature weighted volumetric 2D coronal image as a "guide" for users to find abnormalities in 3D breast ultrasound images more quickly and with less errors, in accordance with the method and system described herein.

BACKGROUND

This invention is in the field of early detection of breast cancer. In the US, the expected statistical figures for breast cancer in 2013 are: approximately 230,000 new cases and 40,000 deaths. The mortality rate would be lowered if breast cancers could be detected in the earlier stage. Screening with X-ray mammography has been the gold standard for the early detection of breast cancer. However, in about 40% of the screening population, where the women have more than 50% of their breasts covered by dense fibro-glandular breast tissues, X-ray mammography has been found to be inadequate in depicting regions of breast covered by the dense breast tissues. Recent clinical studies show that breast ultrasound could be very effective for breasts with dense tissues, particularly automated 3D breast ultrasound. Currently, the only breast ultrasound system that received USFDA approval for breast cancer screening so far is an automated 3D breast ultrasound system using a chestward compression scanning procedure.

The subject matter claimed herein is not limited to embodiments that solve any disadvantages or that operate only in environments such as those described above. Rather, this background is only provided to illustrate one exemplary technology area where some embodiments described herein may be practiced.

SUMMARY

According to some embodiments, a computer workstation system is described for ultrasound examination of a patient's breast. The system includes: a storage system for an image dataset in the form of a plurality of two-dimensional scan images representative of a chestwardly compressed breast sonographically scanned using an automated three-dimensional breast ultrasound acquisition system; a processor configured to: (a) generate a three-dimensional volumetric dataset based on said image dataset; (b) segment and filter said three-dimensional volumetric dataset; and (c) generate a two-dimensional coronal guide image based on the segmented and filtered three-dimensional volumetric dataset, wherein said two-dimensional guide image includes visually enhanced suspected abnormalities within said segmented and filtered three-dimensional volumetric dataset if present in the breast; and an interactive user interface configured to: (a) electronically display to a user said coronal guide image; (b) receive user input indicating a user's selection of a suspected abnormality; and (c) in response to the user's selection displaying one or more of the plurality of two-dimensional scan images corresponding to the selected suspected abnormality.

According to some embodiments, a method and system for processing and displaying breast ultrasound information is provided, wherein a 2D feature weighted volumetric coronal image as a "guide" or "road map" is generated from the 3D ultrasound data volume to represent the 3D dataset with the goal of emphasizing abnormalities within the breast while excluding non-breast structures, particularly those external to the breast such as ribs and chest wall, in accordance with the method and system described herein.

In one preferred embodiment, the 2D feature weighted volumetric guide is displayed in the form of a 2D coronal guide image together with a display as in current commercial automated 3D breast ultrasound systems employing chestward compression scans, where a 2D original axial scan image, and a 2D orthogonal (constructed to be orthogonal to the axial scan) image are displayed with the composite 2D coronal thick-slice image(s). By clicking any exhibited abnormality in the 2D feature weighted volumetric coronal guide, with pre-calculated xyz coordinates, the corresponding abnormality can show up in the 2D coronal thick-slice image as well as at the corresponding locations in the 2D original axial scan image and the orthogonal sagittal image In another preferred embodiment, the 2D coronal guide image is displayed together with just the 2D original axial scan image for the quickest review and a snippet of one or more 2D coronal thick-slices. It is sometimes useful to show the coronal thick-slice image, because readers would like to confirm their assessment by examining the presence of spiculations of a mass nodule that only show in composite coronal thick-slices. The quick review of the 2D axial scan images is done in the manner described above.

In yet another preferred embodiment, the 2D coronal guide image is displayed in inverted polarity. That is, in regular guides, the abnormalities are dark colored on relatively light breast tissue background, and in the inverted polarity guides, the abnormalities are light colored on a relatively dark breast tissue background. A reason is that some readers prefer to read the inverted polarity guides, which resemble mammograms (also with light colored abnormalities on a dark background).

In still another preferred embodiment, the 2D coronal guide image is generated through a process of segmenting away non-breast structure and using a filter to enhance the remaining volumetric breast tissue to make the abnormalities more visible and more prominent.

In yet another preferred embodiment, the filter includes a computer aided detection (CAD) algorithm that can detects and ranks the lesions by likelihood. This is particularly useful for very small abnormalities or lesions that show significant likelihood of being malignant by CAD and yet the above described filter may not be enough to make these small abnormalities visible or prominent in the 2D coronal guide image.

In still another preferred embodiment, additional information is shown with an abnormality such as its size, volume, relative probability, likelihood of being malignant, etc.

In another preferred embodiment, the 2D coronal guide image is displayed on a separate monitor situated adjacent to the display monitor of a commercial automated 3D breast ultrasound system.

In another preferred embodiment, the 2D coronal guide image is displayed on a separate sheet of paper to be viewed with the display monitor of a commercial automated 3D breast ultrasound system.

BRIEF DESCRIPTION OF THE DRAWINGS

To further clarify the above and other advantages and features of the subject matter of this patent specification, specific examples of embodiments thereof are illustrated in the appended drawings. It should be appreciated that these drawings depict only illustrative embodiments and are therefore not to be considered limiting of the scope of this patent specification or the appended claims. The subject matter hereof will be described and explained with additional specificity and detail through the use of the accompanying drawings in which:

DETAILED DESCRIPTION

Figure 1:
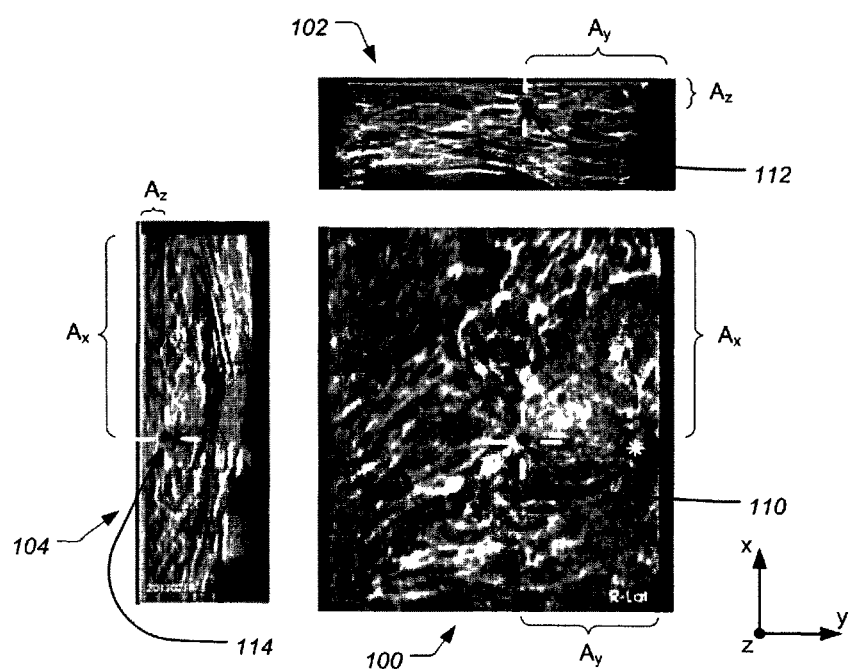
FIG. 1 illustrates aspects of a known commercial system using a 2 mm thick coronal thick-slice as a road map.

A detailed description of examples of preferred embodiments is provided below. While several embodiments are described, it should be understood that the new subject matter described in this patent specification is not limited to any one embodiment or combination of embodiments described herein, but instead encompasses numerous alternatives, modifications, and equivalents. In addition, while numerous specific details are set forth in the following description in order to provide a thorough understanding work, some embodiments can be practiced without some or all of these details. Moreover, for the purpose of clarity, certain technical material that is known in the related art has not been described in detail in order to avoid unnecessarily obscuring the new subject matter described herein. It should be clear that individual features of one or several of the specific embodiments described herein can be used in combination with features or other described embodiments. Further, like reference numbers and designations in the various drawings indicate like elements.

There are two major problems facing any practical breast cancer screening modality. The first major problem of breast cancer screening is the "cost". Since breast cancer has a very low prevalence rate such that one cancer is generally found in 200 to 300 patients screened, the per patient screening cost must be kept low, typically to the range of $100-$200, in order to achieve a reasonable cost per cancer detected. This cost range is generally translated into limiting reading/interpretation time to about 3 minutes per patient and an automated scanning system with a throughput of over 2,000 patients per year. For screening X-ray mammography, where only 4 new images are generated per patient, this 3-minute interpretation time requirement is relatively easily met. However, for breast ultrasound screening, where over 1,200 to 3,000 new images are generated per patient, the 3 minutes of reading/interpretation time limit becomes a real challenge.

The second major problem of breast cancer screening is the "oversight", where obvious cancers are overlooked during the reading/interpretation. The delay in the cancer detection due to oversight would generally cause the cancer to progress to a more advanced stage resulting in increases in treatment cost and decrease in patient survivability. This problem is particularly serious when trying to read/interpret quickly. In a study on blind re-reading by 5 breast radiologists of 427 prior screening mammograms, which were taken a year before the cancer detection, published in Radiology in 2000 (by Warren-Burhenne et al, Vol. 215, pages 554-562), reports that as many as 115 (or 27%) of these prior mammograms were detected by all 5 radiologists and thus should be classed as oversights. In order to reduce the oversight problem, commercial computer-aided diagnosis (CAD) systems have been developed for X-ray mammography screening. Development of clinically useful CAD was no trivial matter, as the CAD must achieve sensitivities close to that of human readers. The development was undertaken by several commercial firms, some in collaboration with universities and national laboratories, over many years and consumed over $100 million in combined developmental cost. The CAD's impact was clearly visible. After 10 years of its commercial introduction, as reported by a study published in JACR in 2010 (by Rao et al, Vol. 7, pages 802-805) that, by year 2008, 75% of the screening mammograms were read with CAD.

The commercial automated 3D breast ultrasound systems all perform chestward compression scans. That is, the ultrasound beam is generally directed chestward during the scan while the breast is generally compressed chestward. This method has many advantages over the earlier non chestward-compressed ultrasound scanning methods such as the method that clamps the breast between a vise-like scanning plates, as in the case of mammography. Namely, the advantages are: patient comfort is much better, the breast tissue is thinner during the scan, and high higher ultrasound frequency could be employed resulting in much better image quality. This is chestward compressed scan method is described more in details in U.S. Pat. No. 7,828,733, which also taught the use of a composite 2D coronal thick-slice method that could be used as a guide or road map to aid the more rapid search for abnormalities. Instead of searching through 300 scanned 2D images in a typical scan of the breast, the reader now searches through far fewer coronal 2D thick-slice images. The coronal thick-slice thickness range was 2-20 mm as stated in the claims of U.S. Pat. No. 7,828,733, but the Figures (e.g. FIGS. 17, 18, 19, 20, 23, and 25) of U.S. Pat. No. 7,828,733 all showed thickness ranges of 6-8 mm as six such thick-slices were sufficient to cover the entire chestward compressed breast. This composite coronal thick-slice road map image has been proven to be very useful and is used in all current commercial automated 3D breast ultrasound systems. However, in all current commercial systems, the most popular coronal thick-slice thickness is in the range of 0.5 mm to 2 mm, resulting in 15 to 60 2D coronal thick-slice images per scan (or 3 to 10 fold increase in the number of 2D coronal thick-slice images as taught by U.S. Pat. No. 7,828,733). The reason for such thickness selection is better image quality and less chance to miss smaller lesions or abnormalities. There will be more discussions in the following parts of this specification on composite coronal thick-slice guide and its comparison with the present invention.

In commercial automated 3D breast ultrasound screening systems using chestward compression scans, for each patient, two to five scans would typically be made on each breast. Each typical scan would generate 300 new images. Thus, 1,200 to 3,000 new images total would typically be generated for each patient. With the 300 to 700 fold increase in the number of new images over screening mammography, one could see that efficient methods and systems must be developed to better manage both the reading/interpretation time as well as the oversight problems before breast ultrasound screening could be broadly employed. Indeed, since the worldwide commercial introduction of automated 3D breast ultrasound using chestward compression several years ago, radiologists at hundreds of facilities around the world have been struggling to read/interpret the huge volume of breast ultrasound images. At the present time, the best readers, even using the composite 2 mm coronal thick-slice image as a road map, could barely reach the 3 minutes limit per patient, while the majority of the readers are averaging more than 5 minutes per patient. There have been no published studies on the "oversight" in automated 3D breast ultrasound yet, but one could venture to guess that the oversight rate could not have been below that found for screening mammography, which is 27%. It is not a surprise that these readers have uniformly been, in the past years, asking researchers to develop some methods and/or systems that could both speed up the reading and reduce the oversight.

In view of the above, an interactive user interface method and system are described for viewing large number of new images within a time limit of 3 minutes and with low oversight.

FIG. 1 illustrates aspects of a known commercial system using a 2 mm thick coronal thick-slice as a road map. FIG. 1 illustrates a prior art road map in the form of currently used commercial "composite coronal thick-slice" method for the reading/interpreting of the 3D breast ultrasound images.

FIG. 1 illustrates a prior art road map in the form of currently used commercial "composite coronal thick-slice" method for the reading/interpreting of the 3D breast ultrasound images. The current commercial automated 3D breast ultrasound systems typically use a thick-slice 100 having a thickness of 2 mm (range around 0.5 to 2 mm), although the U.S. Pat. No. 7,828,733 discussed a range of 2-20 mm when first filed in 2004. Moving to thinner and thinner thickness with commercial systems means that readers must search through more thick slices, e.g., 20 to 30 composite coronal thick-slices per scan currently, although it can be a 10× reduction of search volume vs. the raw 2D axial scan images. In the meantime, readers at hundreds of facilities may still struggle to reach the 3-minute read time limit. In contrast to that, this patent specification teaches a method and a system in which only one composite coronal guide image for each scan can be sufficient. Most of the scans actually show no abnormalities resulting in substantial decrease in the read time. With the addition of CAD, the oversight problem for ultrasound breast imaging should also be reduced. Also shown in FIG. 1 is the original axial 2D image 102 and constructed orthogonal 2D image 104. After searching through many 2D coronal images such as 100, the user finds abnormality 110 in image 100. Clicking on abnormality 110 in image 100 (with a location of $A_x, A_y, A_z$), automatically brings up corresponding abnormalities 112 and 114 in images 102 and 104 respectively.

Figure 2:
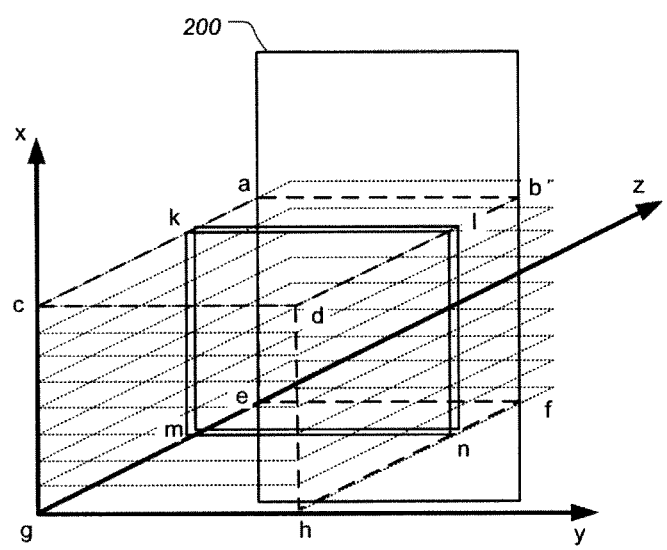
FIG. 2 illustrates aspects of chestward compression scan orientation in relationship to a 2D coronal thick-slice according to prior art, as well as a volume from which a 2D coronal volumetric guide is derived, according to some embodiments.

FIG. 2 illustrates aspects of chestward compression scan orientation in relationship to a 2D coronal thick-slice according to prior art, as well as a volume from which a 2D coronal volumetric guide is derived, according to some embodiments. FIG. 2 illustrates chestward compression scan orientation in relationship to a 2D coronal thick-slice guide (k,l,m,n) and the volume (a,b,c,d,e,f,g,h) from which the 2D coronal volumetric guide is derived. Chestwall 200 is shown. The planes a,b,c,d to e,f,g,h are the original axial scanned images.

Figure 3:
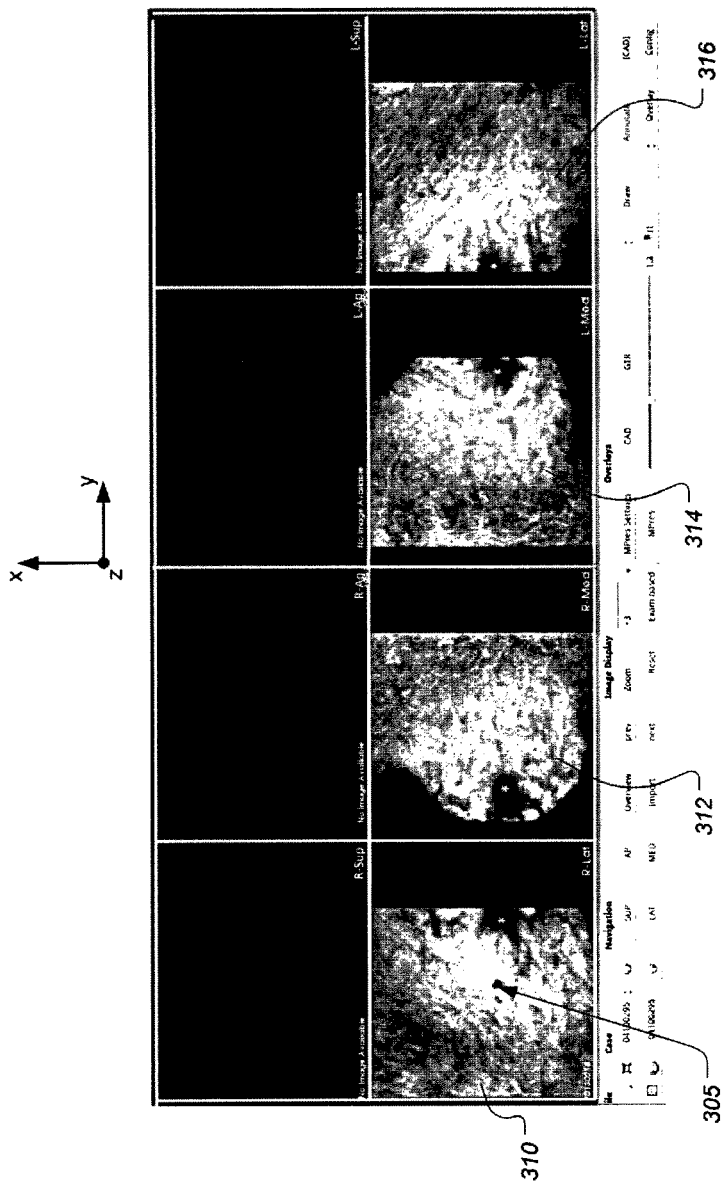
FIG. 3 illustrates aspects of a start up screen with four coronal guide images, according to some embodiments.

FIG. 3 illustrates aspects of a start up screen with four coronal guide images, according to some embodiments. FIG. 3 illustrates a typical startup screen of the workstation after a patient scan by the automated 3D ultrasound breast system, which screen shows a set of coronal guide images, one corresponds to each scan. Although in this patient there are only 2 scans per breast, current commercial systems may take up to 5 scans per breast. The most prominent abnormality is on the R-Lat coronal guide image.

FIG. 3 illustrates a typical startup screen of the workstation after a patient scan by an automated 3D ultrasound breast system, which shows a set of coronal guide images 310, 312, 314 and 316, with one guide image corresponding to each scan. Although there could be 5 scans per breast, FIG. 3 shows just 2 scans per breast for this patient. The most prominent abnormality, 305, is on the R-Lat coronal guide image.

Figure 4:
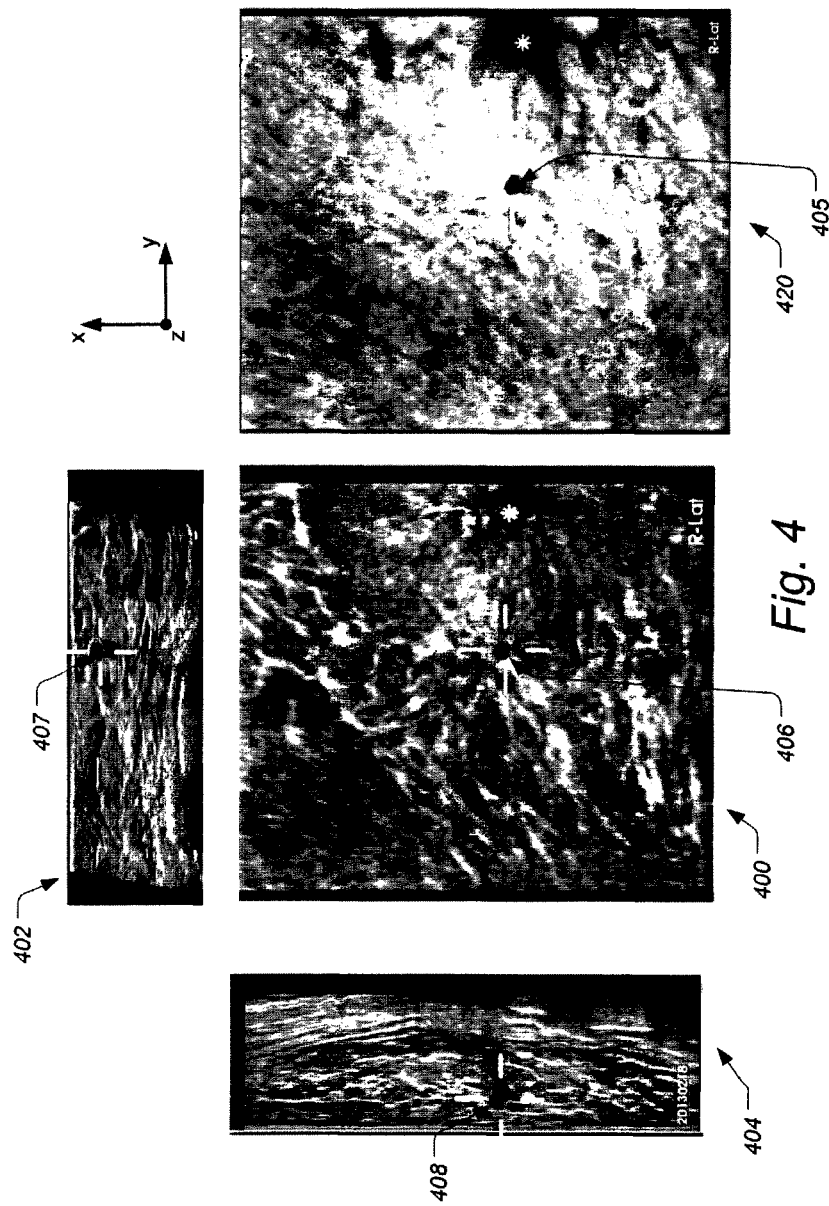
FIG. 4 illustrates aspects of a displayed coronal guide image, an original 2D axial slice, an orthogonal 2D slice, and a coronal thick-slice, according to some embodiments.

FIG. 4 illustrates aspects of a displayed coronal guide image, an original 2D axial slice, an orthogonal 2D slice, and a coronal thick-slice, according to some embodiments. FIG. 4 illustrates a screen resulting after clicking the prominent abnormality 405 in the R-Lat coronal guide image 420. Since the xyz coordinates have been previously computed, the click on 405 immediately brings up the corresponding abnormality 406 in 2-D coronal thick-slice 400. Also, the corresponding abnormality 407 in the axial image 402 as well as abnormality 408 in the orthogonal image 404. X-direction is the axial direction, usually parallel to the patient's head-to-toe direction, and is also the direction of the linear ultrasound scanning. Y-direction is parallel to the patient's left-right direction. Z-direction is the chestward direction. The reader, in most cases a radiologist, can quickly review the 2D axial scan images by activating the scroll bar in the guide and scroll through the axial images. Likewise, the orthogonal images can be reviewed quickly by activating the corresponding scroll bar. A blank coronal guide image can mean the absence of any significant or prominent abnormalities in the guide image and the associated 3D breast volume.

FIG. 4 illustrates what happens after clicking the prominent abnormality in the R-Lat coronal guide image. Since the xyz coordinates have been previously computed, the click immediately brings up the corresponding abnormality in the axial image as well as in the orthogonal image. X-direction is the axial direction, usually parallel to the patient's head-to-toe direction, and is also the direction of the linear ultrasound scanning. Y-direction is parallel to the patient's left-right direction. Z-direction is the chestward direction. The reader, in most cases a radiologist, can quickly review the 2D axial scan images by activating the scroll bar in the guide and scroll through the axial images. Likewise, the orthogonal images can be reviewed quickly by activating the corresponding scroll bar. A blank coronal guide image can mean the absence of any significant or prominent abnormalities in the guide image and the associated 3D breast volume.

Figure 5:
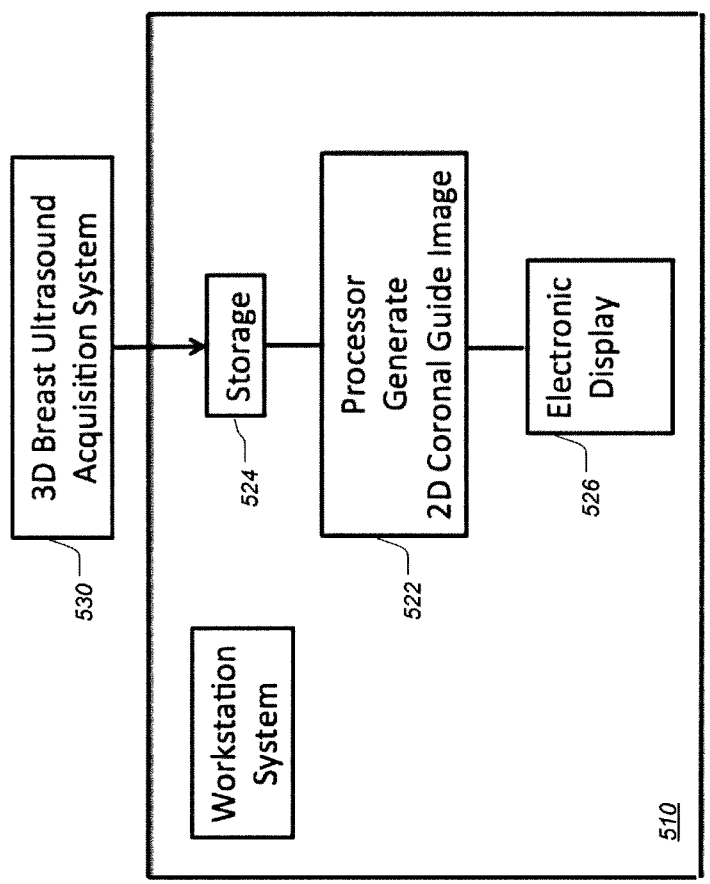
FIG. 5 is a diagram illustrating aspects of a system for generating and displaying a two-dimensional corona guide image, according to some embodiments.

FIG. 5 is a diagram illustrating aspects of a system for generating and displaying a two-dimensional coronal guide image, according to some embodiments. FIG. 5 illustrates a block diagram of a workstation system for the storage of data, processing to generate display the 2D Coronal guide image for the reading/interpreting of the 3D breast ultrasound images according to a preferred embodiment.

FIG. 5 illustrates in block diagram form a workstation system 510 for the storage of data and processing to generate display the 2D Coronal guide image for the reading/interpreting of the 3D breast ultrasound images according to a preferred embodiment. Shown in workstation 510 is storage 524, processor 522 for generating 2-D coronal guide image, and a display 526. Also shown the 3-D breast ultrasound acquisition system 530 as the source of 3D ultrasound data.

Figure 6:
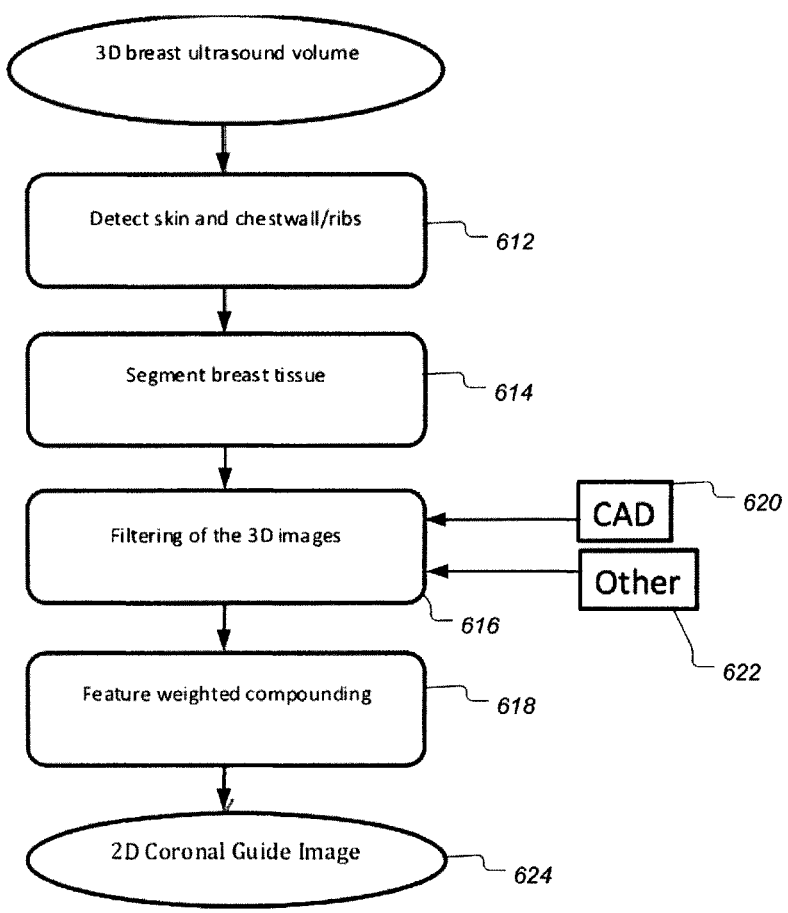
FIG. 6 is a flow chart illustrating aspects of generating and displaying a two-dimensional coronal guide image, according to some embodiments.

FIG. 6 is a flow chart illustrating aspects of generating and displaying a two-dimensional coronal guide image, according to some embodiments. FIG. 6 illustrates a process flow leading to the generation of the 2D Coronal guide image.

FIG. 6 illustrates a flow process in generating the 2D coronal guide image. The flowchart illustrates an algorithm that can be used in each module, such as breast tissue segmentation or chestwall/rib detection. First, in step 612, the skin, chest-wall and ribs are detected. In step 614, the region containing only breast tissue is segmented. Skin region can be simply defined as the region within certain distance range from the top, say 0 to 2 mm. In the Filtering step 616, the 3D volume image is filtered by a group of filters that are designed to suppress noise and artifacts and enhance lesions. As an example, the filters can be a gradient conversion filter and a line conversion filter. The gradient conversion filter is designed to enhance the dark rounded shapes and the line conversion filter is designed to enhance lines radiating from a center which resemble a speculation or architectural distortion. Another example of the filter can be a computer aided detection (CAD) algorithm 620 that can detects and rank the lesions by likelihood. Other filters 622 can be derived from techniques such as minimum voxel value, Doppler data, and/or elastography data.

The weights, w(x, y, z) for compounding are generated by combining the outputs of the filters.

$$w(x, y, z) = \sum_{i}^{N} k_i f_i(x, y, z)$$

Where N is the total number of filters, $f_i(x, y, z)$ is the output of fth filter and $k_i$ is a constant scaling factor for fth filter. The weight is also normalized from 0 to 1 as the probability of a voxel overlap with a cancer lesion.

The atlas image a(x, y) is generated by projecting the volumetric image along the z direction (excluding skin, chestwall and rib regions) modulated by the weight. The equation below shows one example of the projection by taking the minimum value of the weighted intensity alone the z axis.

$$a(x,y) = \text{MIN}_{across\ z}(I(x,y,z)(1-w(x,y,z)))$$

Where I(x, y, z) is the intensity or voxel value of the 3D ultrasound volumetric image.

Figure 7:
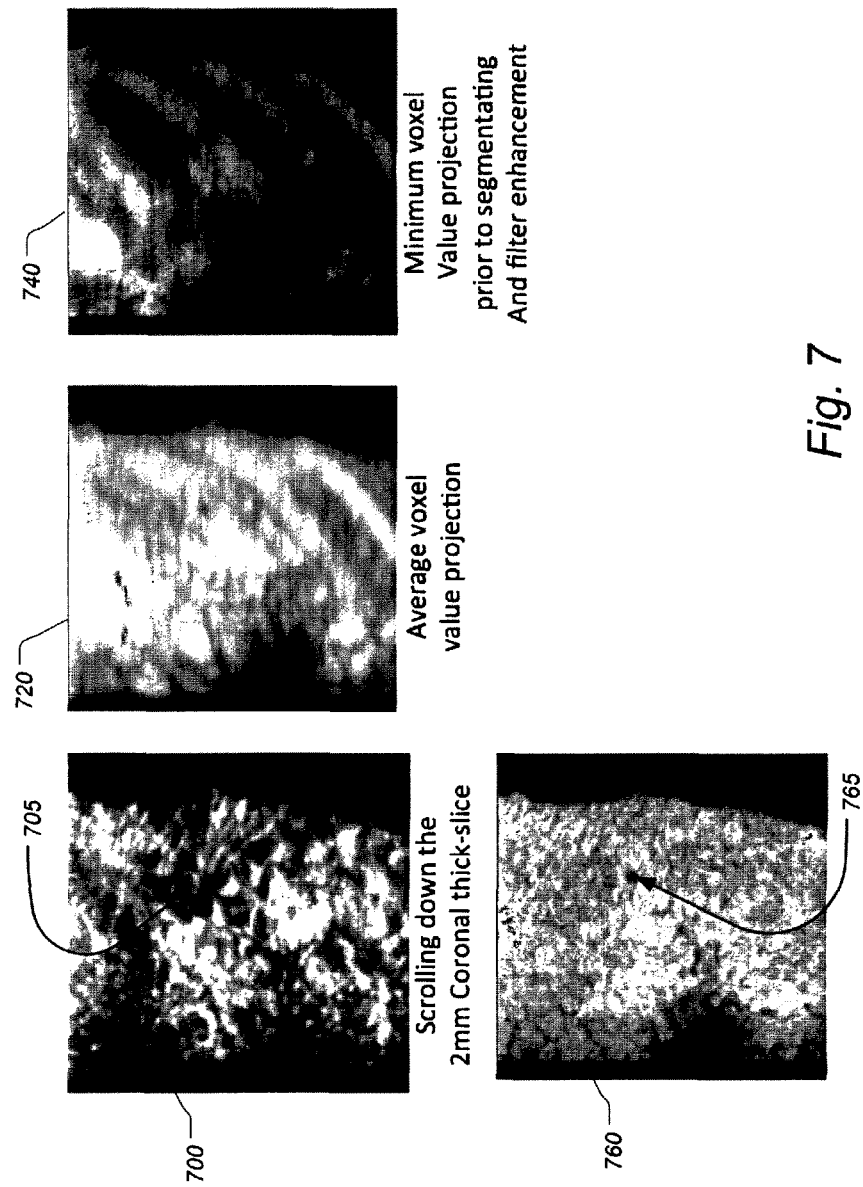
FIG. 7 illustrates effects of segmenting non-breast structures and filter enhancement of a minimum voxel value projection; according to some embodiments.

FIG. 7 illustrates effects of segmenting non-breast structures and filter enhancement of a minimum voxel value projection; according to some embodiments. FIG. 7 illustrates effects of segmenting and filter enhancement of coronal image.

FIG. 7 illustrates the profound effect of segmentation and filter enhancement of volumetric coronal image. 700 shows a 2 mm 2D coronal thick-slice image. After searching by scrolling through approximately 30 such images in the chestward (z-direction) direction, a cancer like abnormality 705 is found. 720 shows the volumetric compounding by showing the 2D coronal image of average voxel value projection average, by taking the average voxel value alone the z direction (perpendicular to the coronal image plane and chestwall) of the breast. The cancer like abnormality is not visible in this image. 740 shows a similar projection along the z-direction using the minimum voxel value. Again, the cancer like abnormality is not visible. 760 shows the minimum voxel value volumetric projection after segmenting non-breast tissues and application of filter enhancement, which process has been described above. The cancer like abnormality 765 is now very visible.

Figure 8:
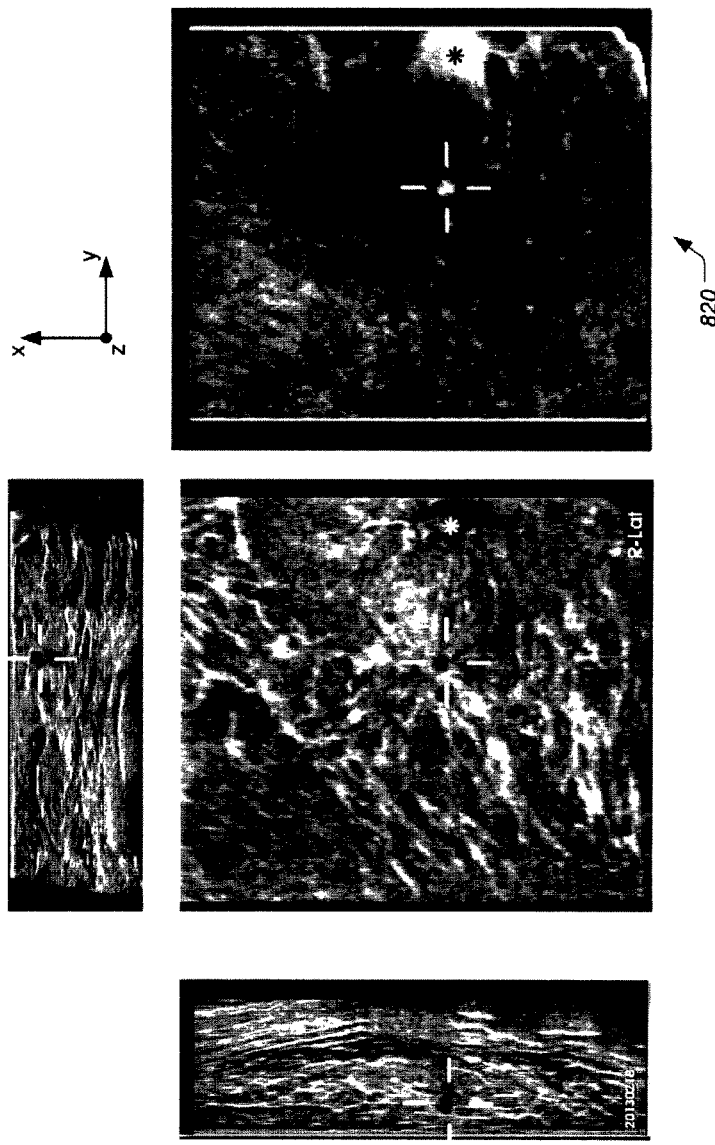
FIG. 8 illustrates aspects of a displayed inverted coronal guide image along with an original 2D axial slice, an orthogonal 2D slice, and a coronal thick-slice, according to some embodiments.

FIG. 8 illustrates aspects of a displayed inverted coronal guide image along with an original 2D axial slice, an orthogonal 2D slice, and a coronal thick-slice, according to some embodiments. FIG. 8 illustrates a 2D coronal guide image 820 in reverse polarity, which some readers may prefer.

Figure 9:
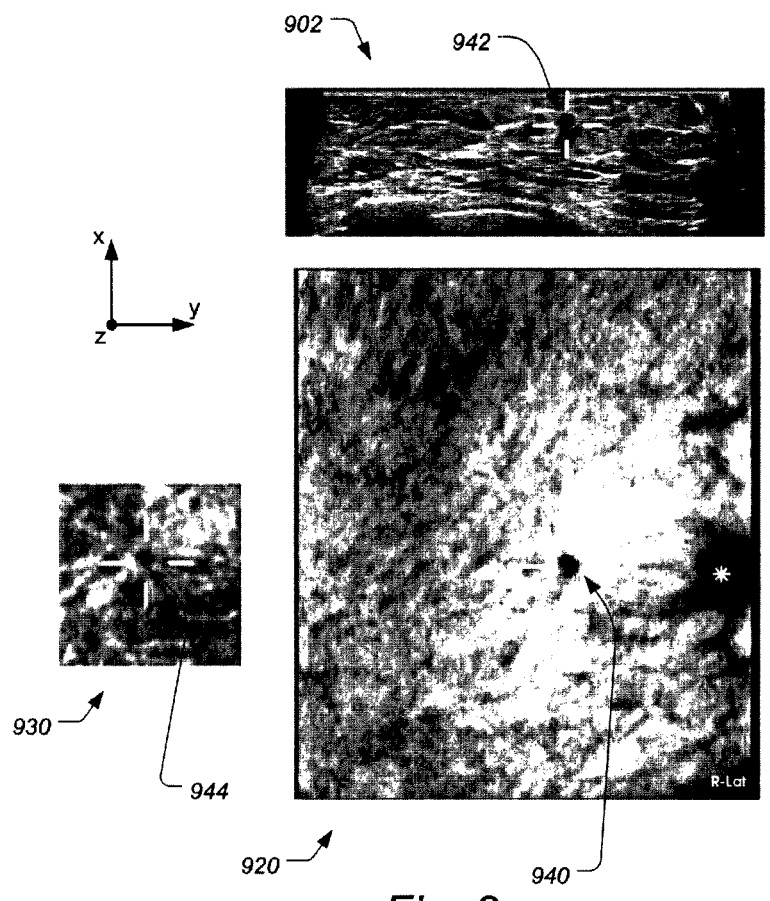
FIG. 9 illustrates aspects of a displayed coronal guide image along with an original 2D axial slice with a snippet of a coronal thick slice, according to some embodiments.

FIG. 9 illustrates aspects of a displayed coronal guide image along with an original 2D axial slice with a snippet of a coronal thick slice, according to some embodiments. FIG. 9 illustrates an example with fewer display components, including the 2D coronal guide, just one set of 2D images from the scan for review and scroll review, and a snippet or whole of the 2D coronal thick-slice. The display of the 2D coronal thick-slice may be useful because readers may like to confirm their assessment by examining the presence of spiculations of the mass nodule which only show in the 2D composite coronal thick-slices.

FIG. 9 illustrates an example with fewer display components, including the 2D coronal guide 920, just one 2D image 902 from the scan for review and scroll review, and a snippet 930 or whole of the 2D coronal thick-slice. The display of the 2D coronal thick-slice may be useful because readers may like to confirm their assessment by examining the presence of spiculations of the mass nodule which only show in the 2D composite coronal thick-slices. Clicking the abnormality 940 in guide image 920 automatically brings up the corresponding abnormalities 942 and 944 in images 902 and snippet 930, respectively.

Although the foregoing has been described in some detail for purposes of clarity, it will be apparent that certain changes and modifications may be made without departing from the principles thereof. It should be noted that there are many alternative ways of implementing both the processes and apparatuses described herein, including for using the described devices or certain aspects thereof for hysteroscopy but not for endometrial biopsy, or for endometrial biopsy but not for hysteroscopy, or for endoscopy and/or biopsy other than of the uterus. For example, in some applications the device shown in FIGS. 50-51 could also be used for taking fluid and/or fluid/tissue endometrial samples through the forward facing fluid parts. Accordingly, the present embodiments are to be considered as illustrative and not restrictive, and the body of work described herein is not to be limited to the details given herein, which may be modified within the scope and equivalents of the appended claims.

What it claimed is:

1. A method of operating an ultrasound breast imaging system, comprising:
   acquiring a three-dimensional (3D) breast ultrasound image with a 3D breast ultrasound acquisition system by a chestward compression scan of a patient's breast;
   detecting skin, chestwall, and ribs in the 3D ultrasound image with a computer processor;
   segmenting a portion of the 3D breast ultrasound image that excludes the detected skin, chestwall, and ribs;
   filtering the segmented portion of the 3D breast ultrasound image to suppress noise and enhance lesions therein by using a computer processor to apply thereto a gradient conversion filter f1 that enhances dark rounded shapes in the breast, a line conversion filter f2 that enhances lines radiating from a center and resemble a speculation or architectural distortion in the breast, and a computer-aided detection filter f3 algorithm, and generating compounding weights w(x,y,z) by combining outputs of the filters f1, f2, and f3, where (x,y,z) designates respective 3D locations of voxels in the segmented portion of the 3D ultrasound image;
   normalizing the weights w(x,y,z) for a probability of voxel overlap with a cancer lesion;
   producing only one composite coronal guide two-dimensional (2D) image for said chestward compression scan of the breast by forming a 2D atlas image through projecting, with a computer processor, the segmented portion of the 3D breast ultrasound image modulated by the normalized compounding weights w(x,y,z);
   displaying the composite coronal guide 2D image on a computer monitor coupled with the computer processor; and
   causing the computer processor to respond to pointing to a lesion in the displayed composite coronal guide 2D image to automatically bring up on the display an additional image from said chestward compression scan, which additional image contains the pointed to lesion.

2. The method of claim 1, in which said additional image is an original 2D axial slice image taken in said acquiring step.

3. The method of claim 1, in which the acquiring step takes additional 3D breast ultrasound images by additional chestward compression scans of the patient's breast, and the remaining steps of the method are applied to each of the additional images, thereby producing and displaying a respective single composite coronal guide 2D image for each of said additional chestward compression scans.

* * * * *